United States Patent [19]

Shaw

[11] Patent Number: 5,618,981

[45] Date of Patent: Apr. 8, 1997

[54] PROCESS FOR PRODUCING AROMATIC SULFIDES

[75] Inventor: James E. Shaw, Bartlesville, Okla.

[73] Assignee: Phillips Petroleum Company, Bartlesville, Okla.

[21] Appl. No.: 445,262

[22] Filed: May 19, 1995

[51] Int. Cl.$^6$ .................................................. C07C 319/14
[52] U.S. Cl. .............................. 568/44; 562/76; 562/426; 568/29; 568/41; 568/42; 568/56
[58] Field of Search .................................. 568/44, 29, 41, 568/42, 56; 562/76, 426

[56] References Cited

U.S. PATENT DOCUMENTS

| | | | |
|---|---|---|---|
| 2,986,573 | 5/1961 | Topliss | 167/65 |
| 3,775,131 | 11/1973 | Hendriks et al. | 96/91 R |
| 3,992,432 | 11/1976 | Napier et al. | 260/465.1 |
| 4,287,125 | 9/1981 | Soula | 568/44 |

OTHER PUBLICATIONS

Rubin et al, Science, vol. 133, p. 2067 (Jun. 30, 1961).

*Primary Examiner*—D. R. Wilson
*Attorney, Agent, or Firm*—Lucas K. Shay

[57] ABSTRACT

A process which can be used to produce an aromatic sulfide compound having the formula of $(R_{4-n})(X_n)(W)Ar-S-R'$ is provided. The process comprises contacting, in the presence of a surfactant, a halo-substituted aromatic compound in an aqueous solution with a salt of a mercaptan under conditions sufficient to produce the aromatic sulfide in which the halo-substituted aromatic compound and salt of mercaptan are each present in an amount effective to synthesize the aromatic sulfide wherein R is hydrogen or a hydrocarbyl radical, X is a hlogen, n is a number from 0 to 3, W is a substituent, Ar is an aromatic ring, and R' is a hydrocarbyl radical.

23 Claims, No Drawings

PROCESS FOR PRODUCING AROMATIC SULFIDES

FIELD OF THE INVENTION

The present invention relates to a process for producing an aromatic sulfide from a halo-substituted aromatic compound and a salt of a mercaptan.

BACKGROUND OF THE INVENTION

Aromatic sulfides such as nitrophenyl sulfides are generally a class of chemicals used as intermediates for the synthesis of other chemicals. For example, 2-chloro-6-nitrophenyl isopropyl sulfide or 2-chloro-6-nitrophenylthio-isopropyl ether can be used to synthesize agricultural chemicals and 3-chloro-6-nitrophenyl benzyl sulfide (2-benzylthio-4-chloronitrobenzene) can be used to synthesize diazoxide which is used as antihypertensive agent for reducing high blood pressure.

Generally, nitrophenyl sulfides can be made from halo-substituted aromatic compounds in displacement reactions. In the displacement reactions, nucleophiles having a sulfur atom are capable of displacing an electronegative halogen group from the aromatic compounds thereby forming a bond with electron-deficient carbon of the aromatic compounds. For example, it has been reported that 6-nitrophenyl benzyl sulfide is synthesized by reacting 2,4-dichloro nitrobenzene with benzyl mercaptan in the presence of potassium hydroxide in ethanol solution. Such synthetic route requires the use of an organic solvent.

Attempts to synthesize an aromatic sulfide such as a nitrophenyl sulfide without using an organic solvent were unsuccessful because the reaction rate was slow, the conversion of reactants was low, many by-products were formed, the yield was low, and the purity of the product was also low. Therefore there is a need to develop an improved process for producing an aromatic sulfide using an aqueous medium. Development of such a process would also significantly contribute to the art of aromatic sulfide synthesis.

SUMMARY OF THE INVENTION

An object of the present invention is to provide a process for producing an aromatic sulfide without using an organic solvent. Another object of the present invention is to provide a process for producing an aromatic sulfide in high yield and purity. A further object of the present invention is to provide a process for producing an aromatic sulfide which does not require further purification. An advantage of the present invention is that a high conversion of reactants to an aromatic sulfide. Another advantage of the present invention is that the invention process provides a fast reaction rate.

According to the present invention, a process that can be used for producing an aromatic sulfide is provided. The process comprises contacting, in the presence of a surfactant, a halo-substituted aromatic compound with a salt of a mercaptan in an aqueous medium under a condition sufficient to effect the synthesis of an aromatic sulfide where the halo-substituted aromatic compound and the salt of a mercaptan are each present in an effective amount for the synthesis of an aromatic sulfide. A salt of a mercaptan can also be made in-situ by contacting an ammonium hydroxide or a metal hydroxide with a mercaptan.

DETAILED DESCRIPTION OF THE INVENTION

According to the present invention, the term aromatic sulfide is defined as an organic sulfide compound having the formula of $(R_{4-n})(X_n)(W)Ar-S-R'$ wherein each R can be the same or different and is each independently selected from the group consisting of hydrogen, hydrocarbyl radicals, and combinations of any two or more thereof in which the hydrocarbyl radical is selected from the group consisting of alkyl radicals, akenyl radicals, alkaryl radicals, aralkyl radicals, cycloalkyl radicals, cycloalkenyl radicals, and combinations of any two or more thereof; each X is a halogen; n is a number from 0 to 3; W is a substitutent selected from the group consisting of $-NO_2$, $-SO_3H$, $-CHO$, $-COOH$, $-NO$, $-N^+{}_2$, $-CN$, $-COR$, $-COO^-$, $SO_3{}^-$, $-SO_2CH_3$, $-CF_3$, $-N^+(CH_3)_3$, and combinations of any two or more thereof; Ar is a phenyl group, naphthyl group, biphenyl group or combinations of any two or more thereof; R' is selected from the group consisting of alkyl radicals, akenyl radicals, alkaryl radicals, aralkyl radicals, cycloalkyl radicals, cycloalkenyl radicals, R—W, and combinations of any two or more thereof wherein R and W are the same as those disclosed above; and each hydrocarbyl radical has 1 to about 30, preferably 1 to about 20, and most preferably 1 to 15 carbon atoms.

Examples of suitable aromatic sulfides include, but are not limited to, 2-chloro-6-nitrophenyl isopropyl sulfide. 3-chloro-6-nitrophenyl benzyl sulfide, 3-chloro-6-nitrophenyl isopropyl sulfide, 4-chloro-6-nitrophenyl isopropyl sulfide, 2-chloro-6-nitrophenyl methyl sulfide, 3-chloro-6-nitrophenyl methyl sulfide, 4-chloro-6-nitrophenyl methyl sulfide, 2-chloro-6-nitrophenyl benzyl sulfide, 4-chloro-6-nitrophenyl benzyl sulfide, 3-chloro-6-nitrophenyl cyclohexyl sulfide. 4-nitrophenyl methyl sulfide, 4-nitrophenyl isopropyl sulfide. 4-nitrophenyl benzyl sulfide, 3-nitrophenyl methyl sulfide, 3-nitrophenyl isopropyl sulfide, 3-nitrophenyl benzyl sulfide, 4-benzylthiobenzaldehyde, 4-isopropylthiobenzaldehyde, 3-benzylthiobenzoic acid, 4-methylthiomethylbenzoate, and combinations of any two or more thereof.

The halo-substituted aromatic compound suitable for use in the present invention has a general formula of $(R_{4-n})(X_{n+1})WAr$ wherein R, n, X, W, and Ar are the same as those disclosed above; and it is preferred that one, and only one, X be at the ortho-position to W in the Ar ring.

Examples of suitable halo-substituted aromatic compounds include, but are not limited to, 2,3-dichloronitrobenzene, 3,4-dichloronitrobenzene, 2,4-dichloronitrobenzene, 2,3-difluoronitrobenzene, 3,4-difluoronitrobenzene, 2,4-difluoronitrobenzene, 2,3-dibromonitrobenzene, 3,4-dibromonitrobenzene, 2,4-dibromonitrobenzene, 2,4-dichloro-5-nitrotoluene, 3,4-dichloro-5-nitrobenzene, 4-chlorobenzaldehyde, 4-bromobenzaldehyde, 4-iodobenzaldehyde, 3-chlorobenzaldehyde, 3-bromobenzaldehyde, 4-chlorobenzoic acid, 4-bromobenzoic acid, 3-iodobenzoic acid, 4-chloromethylbenzoate, 4-bromomethylbenzoate, and combinations of any two or more thereof.

These halo-substituted aromatic compounds generally are commercially available or can be made by any methods known to one skilled in the art. Because the methods are well known, description of which is omitted herein for the interest of brevity.

A salt of a mercaptan suitable for use in the present invention can be any salt of any mercaptan so long as the salt can provide a nucleophile for displacing the activated halogen on the halo-substituted aromatic compound. Generally, a salt of a mercaptan has the formula of MSR' wherein M can be an alkali metal ion, an alkaline earth metal ion, ammonium ion, and combinations of any two or more thereof; and R' is the same as that disclosed above.

Alternatively, a salt of a mercaptan can also be prepared in-situ by contacting a halo-substituted aromatic compound with a mercaptan R'SH and either a metal hydroxide MOH or ammonium hydroxide where M and R' are the same as described above.

Examples of suitable salts of mercaptans include, but are not limited to, sodium isopropanethiolate, potassium isopropanethiolate, ammonium isopropanethiolate, calcium isopropanethiolate, sodium benzyl mercaptide, potassium benzyl mercaptide, ammonium benzyl mercaptide, calcium benzyl mercaptide, sodium methanethiolate, sodium ethanethiolate, sodium cyclohexanethiolate, potassium methanethiolate, potassium ethanethiolate, ammonium methanethiolate, ammonium ethanethiolate, and combinations of any two or more thereof.

These suitable salts of mercaptans are either available commercially or can be made by well known methods such as reaction of a mercaptan R'SH with a metal hydroxide MOH, ammonium hydroxide, a base such as, for example, sodium carbonate, sodium bicarbonate, potassium carbonate, potassium bicarbonate, or combinations of any two or more thereof where M and R' are the same as described above. Because these methods are well known to those skilled in the art, the description of which is omitted herein for the interest of brevity.

According to the present invention, an aqueous medium denotes, unless otherwise indicated, a reaction medium which does not contain an organic solvent, for the contact of a halo-substituted aromatic compound and a salt of a mercaptan. However, it can also comprise an organic solvent such as, for example, toluene. Generally, an aqueous medium can comprise regular tap water, deionized water, distilled water, a solution, a suspension, and combinations of any two or more thereof. Presently it is preferred that regular tap water be used because it is readily available and economical. According to the present invention, any surfactant that facilitates the mixing of reactants into substantially a single phase can be used.

Generally, the surfactant comprises one or more compounds which exhibit surface-active properties. A preferred surfactant for use in the reaction system of the instant invention is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of any two or more thereof.

The presently preferred surfactant is an alkoxylated compound. Examples of suitable alkoxylated compounds include, but are not limited to, alkoxylated alcohols, alkoxylated mercaptans, sulfates of alkoxylated alcohols, alkoxylated phenols, sulfates of alkoxylated phenols, and combinations of any two or more thereof.

The alkoxylated alcohol useful in the present invention has a general formula of $R^2O[CH_2CH(R^3)O]_qH$ where $R^2$ is a $C_1$–$C_{20}$ hydrocarbyl radical selected from the group consisting of alkyl radical, alkylaryl radical, aryl radical, cycloalkyl radical, alkenyl radical, and combinations of any two or more thereof; Preferably $R^2$ is a $C_6$–$C_{18}$ alkyl radical. Most preferably $R^2$ is a $C_{10}$–$C_{16}$ alkyl radical; $R^3$ is selected from the group consisting of hydrogen, $C_1$–$C_{16}$ alkyl radicals, $C_2$–$C_{16}$ alkenyl radicals, and combinations of any two or more thereof; and q is a number of from 1 to about 20, preferably from about 2 to about 12, most preferably from 5 to 10. Generally $R^3$ can contain from 0 to about 16 carbon atoms. Preferably $R^3$ is a hydrogen or a $C_1$–$C_3$ alkyl radical. Most preferably $R^3$ is hydrogen. An example of suitable alkoxylated alcohol is TERGITOL® 15-S-7 which is an ethoxylated alcohol, is manufactured and marketed by Union Carbide Corporation, and has the formula of $R^2O(CH_2CH_2O)_7H$ where $R^2$ is a secondary alkyl radical having 11–15 carbon atoms and 7 is the averaged number of the ethylene oxide units. Another example is an ethoxylated phenol having the same number of ethylene oxide units. Other suitable alkoxylated alcohols are also available from Union Carbide Corporation.

The sulfate of alkoxylated alcohol useful in the present invention has a general formula of $R^2O[CH_2CH(R^3)O]_qSO_3M$ where $R^2$, $R^3$, and q are the same as those described above and M is an alkali metal or an alkaline earth metal or combinations of any two or more thereof. An example of suitable sulfate of alkoxylated alcohol is sodium sulfate of an ethoxylated alcohol having the formula of $R^2O(CH_2CH_2)_qSO_3Na$ in which $R^2$ and q are the same as those disclosed above.

Useful alkoxylated phenols and sulfates of alkoxylated phenols can have general formulas of $(R^3)_pAr'O[CH_2CH(R^3)O]_qH$ and $(R^2)_pAr'O[CH_2CH(R^3)]_qSO_3M$, respectively where $R^2$, $R^3$, q and M are the same as those disclosed above, Ar' is a phenyl group and p is an integer ranging from 0 to 5. Examples of these alkoxylated phenols are ethoxylated phenol $Ar'O(CH_2CH_2O)_qH$ and sodium sulfate of ethoxylated phenol $Ar'O(CH_2CH_2O)_qSO_3Na$ where Ar and q are the same as disclosed above.

The alkoxylated mercaptan useful in the present invention has a general formula of $R^2S[CH_2CH(R^3)O]_qH$ where $R^2$, $R^3$, and q are the same as those described above. An example of an alkoxylated mercaptan is an ethoxylated mercaptan having the formula of $R^2S(CH_2CH_2O)_7H$ where $R^2$ is primarily a tertiary dodecyl group and 7 is the averaged number of ethylene oxide units. This ethoxylated mercaptan is a surfactant, commercially available from Phillips Petroleum Company, Bartlesville, Okla. under the trade name AQUA-CLEEN® II. Another example is an ethoxylated thiophenol having the same number of ethylene oxide units. Other suitable alkoxylated mercaptans are also available from Phillips Petroleum Company.

Quaternary ammonium salt useful in the present invention has the general formula $(R^4)_4N^+X^-$ where $R^4$ is an alkyl radical of from 1 to 20 carbon atoms; and X is selected from the group consisting of $Br^-$, $Cl^-$, $I^-$, $F^-$, $R^4CO_2^-$, $QSO_3^-$, $BF_4^-$, and $HSO_4^-$, where Q is an aryl, alkaryl or arylalkyl radical of 6 to 10 carbon atoms. It will be noted that a variety of anions are suitable as the component of the quaternary ammonium salts.

Useful quaternary ammonium salts according to the general formula given above include, but are not limited to, methyltrialkyl($C_8$–$C_{10}$)ammonium chloride (also known as Adogen® 464), cetyltrimethylammonium bromide, hexadecyltrimethylammonium bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutyl ammonium fluoride, tetrabutylammonium tetrafluoroborate, and combinations of any two or more thereof.

An alkali metal alkyl sulfate of the general formula of $R^4OSO_3M$ can be used in the present invention, wherein $R^4$ and M are the same as those disclosed above. Examples of suitable compounds according to the general formula for the alkali metal alkyl sulfates include, but are not limited to, lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and combinations of any two or more thereof.

Useful alkali metal salts of alkanoic acids have the general formula of $R^4CO_2M$, where $R^4$ and M have the same meaning as given above. Examples of suitable alkali metal salts of alkanoic acids include, but are not limited to, lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and combinations of any two or more thereof.

Useful alkali metal salts of alkaryl sulfonic acids have the general formula of $(R^4)_pArSO_3M$ where $R^4$ and M are the same as those disclosed above, Ar is a phenyl group, and p is an integer ranging from 0 to 5.

Typical compounds within the group include, but are not limited to, sodium dodecylbenzenesulfonate, potassium dodecylbenzenesulfonate, lithium dodecylbenzenesulfonate, sodium tetradecylbenzenesulfonate, potassium hexadecylbenzenesulfonate, rubidium dodecylbenzenesulfonate, cesium dodecylbenzenesulfonate, sodium octadecylbenzenesulfonate, potassium octadecylbenzenesulfonate, sodium eicosylbenzenesulfonate, and combinations of any two or more thereof.

Examples of suitable 1-alkyl pyridinium salts include, but are not limited to, 1-dodecylpyridinium para-toluenesulfonate, 1-dodecylpyridinium chloride, 1-hexadecylpyridinium chloride, 1-hexadecylpyridinium paratoluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and combinations of any two or more thereof.

The mole ratio of a halo-substituted aromatic compound to a salt of a mercaptan can vary widely so long as the ratio can effect the synthesis of an aromatic thioether can be in the range of from about 1:1 to about 1:100, preferably from about 1:1 to about 1:15, more preferably about 1:1 to about 1:10, and most preferably 1:1 to 1:5, for best results.

The weight ratio of a halo-substituted aromatic compound to a surfactant can vary widely and can be any ratio that can catalyze reaction of a halo-substituted aromatic compound and a salt of a mercaptan. Generally the ratio can be in the range of from about 100,000:1 to about 1:1, preferably about 10,000:1 to about 2:1, more preferably about 5,000:1 to about 5:1, and most preferably 1,000:1 to 10:1.

Conditions for contacting a halo-substituted aromatic compound with a salt of a mercaptan are any suitable conditions that can result in the synthesis of an aromatic sulfide and can include an ambient temperature in the range of from about 0° C. to about 250° C., preferably from about 10° C. to about 175° C., and most preferably from 25° C. to 150° C., for a time of from about 1 second to about 20 hours, preferably about 1 minute to about 15 hours, and most preferably 10 minutes to 10 hours. The pressure can vary widely from about 0.1 atmosphere to about 30 atmospheres, preferably from about 0.1 atmosphere to about 3 atmospheres.

Upon completion of the contacting, the product can be used as is or can be further processed such as washing with water, separations, sparging with an inert gas, distillation or purification by any methods known to one skilled in the art.

The following examples are provided to further illustrate the practice of the invention and are not intended to limit the scope of the invention of the claims.

EXAMPLE I

This example illustrates one way of practicing the process of the invention.

To a 2 liter, 3-necked flask equipped with a thermowell, magnetic stirring bar, pressure equalizing addition funnel, and condenser with $N_2$ inlet on top it was added 250 g of 2,3-dichloronitrobenzene (melting point 61°–62° C.), 350 g of water, and 5 g of Adogen® 464 (methyltrialkyl($C_8$–$C_{10}$)ammonium chloride, obtained from Aldrich Chemical Co., Inc.). The mixture was heated to 65° C. From the addition funnel was then added an aqueous solution of the sodium salt of isopropyl mercaptan (see below for preparation) at a rate to keep the reaction temperature at 65° C. About 20 minutes were required for the addition and the temperature was easily controlled with some cooling. The mixture was then stirred for 1 hour at 65° C. Stirring was stopped and the phases were allowed to separate at 65° C. The bottom product phase was separated from the top aqueous NaCl phase. The product phase was then washed with 300 ml of water. The aqueous phase again was on top. It was necessary to keep the temperature at 65°–70° C. because the product has a melting point of 62°–66° C. The product layer was sparged with $N_2$ at 2 SCFH (standard cubic feet per hour) at 70° C. for 3 hours to remove water. The final product weighed 302 g (100% yield) and solidified on cooling (melting point 62°–66° C.). The color of the product was orange red. GC analysis revealed that the product purity was 96%. GC analysis was done with a 20 in. by ⅛ in. OV-101 column starting at 50° C. and then 15° C./minute to 215° C. for 10 minutes.

The aqueous solution of the sodium salt of isopropyl mercaptan which was used in the above procedure was prepared as follows. To a one liter 3-necked flask equipped with thermowell, magnetic stirring bar, pressure equalizing addition funnel, and condenser with $N_2$ inlet on top it was added 120 g of 50% NaOH solution and 190 g of water. By the addition funnel it was added 118 g of isopropyl mercaptan over 15 minutes with stirring. The temperature of the stirred solution rose but was easily controlled with cooling. The solution of the sodium salt of isopropyl mercaptan which was protected from air by $N_2$, was used in the above example.

EXAMPLE II

This example illustrates the process of the invention by reverse addition of 2,3-dichloronitrobenzene to a salt of a mercaptan.

To a 2-liter, 3-necked flask equipped with a thermowell, magnetic stirring bar, pressure equalizing addition funnel, and condenser with $N_2$ inlet on top it was added 120 g of 50% NaOH solution, 540 g of water, and 5 g of Adogen® 464. By the addition funnel was added 118 g of isopropyl mercaptan in portions over 15 minutes with stirring. The temperature rose but was easily controlled by cooling. The solution was heated to 65° C. Then 250 g of solid 2,3- dichloronitrobenzene (this could also be added molten, mp 61°–62° C.) was added in portions at a rate, so the reaction mixture stayed at 65° C. About 20 minutes were required for the addition, and the temperature was easily controlled by some cooling. The reaction mixture was stirred for one hour at 65° C. The remainder of the process was the same as described in Example I above. GC analysis showed that the yield of orange red solid product was 100% and the purity of the product was 96%.

EXAMPLE III

This example illustrates the use of a different surfactant for practicing the process of the invention.

The run was carried out the same as that described in Example I except that 25 g of 2,3-dichloronitrobenzene, 35 g of water, and 2.0 g of TERGITOL® 15-S-7 (obtained from Union Carbide Corporation) were used, the sodium salt of isopropyl mercaptan was made from 25 g of water, 6.0 g of NaOH pellets, and 11.8 g of isopropyl mercaptan, and the reaction time was 8 hours. GC analysis showed that the product was obtained in 100% yield with a purity of 95%.

EXAMPLE IV

This example is a comparative example showing that without using a surfactant the reaction rate was slow, the conversion was low, and the product was contaminated with undesired by-products.

The run was carried out the same as that described in Example II with the exception that the surfactant Adogen® 464 was not present in the reaction medium. After 1 hour, the reaction was only 10% complete. The reaction temperature was then increased to 80° C. After 3 hours at 80° C., the reaction was only 50% complete. Even after 6 hours at 80° C., the reaction was only about 65% complete and the product was found to be contaminated with about 10% heavies (i.e., molecular weights higher than the desired product).

The results shown in the above examples clearly demonstrate that the present invention is well adapted to carry out the objects and attain the ends and advantages mentioned was well as those inherent therein. While modifications may be made by those skilled in the art, such modifications are encompassed within the spirit of the present invention as defined by the disclosure and the claims.

That which is claimed:

1. A process for producing an aromatic sulfide comprising contacting, in the presence of a surfactant, a halo-substituted aromatic compound in an aqueous medium with a salt of mercaptan wherein:

said aromatic sulfide compound has the formula of $(R_{4-n})(X_n)(W)Ar-S-R'$;

each R is independently selected from the group consisting of hydrogen, hydrocarbyl radicals each having 1 to about 30 carbon atoms, and combinations of any two or more thereof wherein said hydrocarbyl radical is selected from the group consisting of alkyl radicals, akenyl radicals, aryl radicals, alkaryl radicals, aralkyl radicals, cycloalkyl radicals, cycloalkenyl radicals, and combinations of any two or more thereof;

each X is a halogen;

n is an integer from 0 to 3;

W is a substituent selected from the group consisting of $-NO_2$, $-SO_3H$, $-CHO$, $-COOH$, $\times NO$, $-N^+_2$, $-CN$, $-COR$, $-COO'$, $SO_3^-$, $-SO_2CH_3$, $-CF_3$, and $-N^+(CH_3)_3$;

Ar is selected from the group consisting of naphthyl group, phenyl group, and biphenyl group;

R' is selected from the group consisting of alkyl radicals, akenyl radicals, cycloalkyl radicals, and cycloalkenyl radicals;

said halo-substituted aromatic compound has the formula of $(R_{4-n})(X_{n+1})WAr$;

said salt of mercaptan has the formula of MSR' wherein M is selected from the group consisting of alkali metal ions, alkaline earth metal ions, ammonium ions, and combinations of any two or more thereof; and said surfactant is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of any two or more thereof wherein said alkoxylated compound is selected from the group consisting of alkoxylated mercaptans, alkoxylated phenols, sulfates of alkoxylated phenols, and combinations of any two or more thereof.

2. A process according to claim 1 wherein said hydrocarbyl radical has 1 to 15 carbon atoms, X is chlorine, and n is 1.

3. A process according to claim 1 wherein said aromatic sulfide is selected from the group consisting of 2-chloro-6-nitrophenyl isopropyl sulfide, 3-chloro-6-nitrophenyl isopropyl sulfide, 4-chloro-6-nitrophenyl isopropyl sulfide, 2-chloro-6-nitrophenyl methyl sulfide, 3-chloro-6-nitrophenyl methyl sulfide, 4-chloro-6-nitrophenyl methyl sulfide, 3-chloro-6-nitrophenyl cyclohexyl sulfide, 4-nitrophenyl methyl sulfide, 4-nitrophenyl isopropyl sulfide, 3-nitrophenyl methyl sulfide, 3-nitrophenyl isopropyl sulfide, 4-methylthiomethylbenzoate, and combinations of any two or more thereof.

4. A process according to claim 1 wherein said aromatic sulfide is 2-chloro-6-nitrophenyl isopropyl sulfide.

5. A process according to claim 1 wherein said halo-substituted aromatic compound is selected from the group consisting of 2,3-dichloronitrobenzene, 3,4-dichloronitrobenzene, 2,4-dichloronitrobenzene, 2,3-difluoronitrobenzene, 3,4-difluoronitrobenzene, 2,4-difluoronitrobenzene, 2,3-dibromonitrobenzene, 3,4-dibromonitrobenzene, 2,4-dibromonitrobenzene, 2,4-dichloro-5-nitrotoluene, 3,4-dichloro-5-nitrobenzene, 4-chlorobenzaldehyde, 4-bromobenzaldehyde, 4-iodobenzaldehyde, 3-chlorobenzaldehyde, 3-bromobenzaldehyde, 4-chlorobenzoic acid, 4-bromobenzoic acid, 3-iodobenzoic acid, 4-chloromethylbenzoate, 4-bromomethylbenzoate, and combinations of any two or more thereof.

6. A process according to claim 1 wherein said halo-substituted aromatic compound is 2,3-dichloronitrobenzene.

7. A process according to claim 1 wherein said salt of mercaptan is selected from the group consisting of sodium isopropanethiolate, potassium isopropanethiolate, ammonium isopropanethiolate, calcium isopropanethiolate, sodium methanethiolate, sodium ethanethiolate, sodium cyclohexanethiolate, potassium methanethiolate, potassium ethanethiolate, ammonium methanethiolate, ammonium ethanethiolate, and combinations of any two or more thereof.

8. A process according to claim 1 wherein said salt of mercaptan is sodium isopropanethiolate.

9. A process according to claim 1 wherein said aqueous medium is water.

10. A process according to claim 1 wherein said surfactant is a quaternary ammonium salt.

11. A process according to claim 1 wherein said surfactant is methyltrialkyl($C_8$–$C_{10}$)ammonium chloride which is also known as Adogen® 464.

12. A process according to claim 1 wherein:

said aromatic sulfide is selected from the group consisting of 2-chloro-6-nitrophenyl isopropyl sulfide, 3-chloro-6-nitrophenyl benzyl sulfide, 3-chloro-6-nitrophenyl isopropyl sulfide, 4-chloro-6-nitrophenyl isopropyl sulfide, 2-chloro-6-nitrophenyl methyl sulfide, 3-chloro-6-nitrophenyl methyl sulfide, 4-chloro-6-nitrophenyl methyl sulfide, 3-chloro-6-nitrophenyl cyclohexyl sulfide, 4-nitrophenyl methyl sulfide, 4-nitrophenyl isopropyl sulfide, 3-nitrophenyl isopropyl sulfide, and combinations of any two or more thereof, or said halo-substituted aromatic compound is selected from the group consisting of 2,3-dichloronitrobenzene, 3,4-dichloronitrobenzene, 2,4-dichloronitrobenzene, 2,3-difluoronitrobenzene, 3,4-difluoronitrobenzene, 2,4-difluoronitrobenzene, 2,3-dibromonitrobenzene, 3,4-dibromonitrobenzene, 2,4-dibromonitrobenzene, 2,4-dichloro-5-nitrotoluene, 3,4-dichloro-5-nitrobenzene, 4-chlorobenzaldehyde, 4-bromobenzaldehyde, 4-iodobenzaldehyde, 3-chlorobenzaldehyde, 3-bromobenzaldehyde, 4-chlorobenzoic acid, 4-bromobenzoic acid, 3-iodobenzoic acid, 4-chloromethylbenzoate, 4-bromomethylbenzoate, and combinations of any two or more thereof;

said salt of mercaptan is selected from the group consisting of sodium isopropanethiolate, potassium isopropanethiolate, ammonium isopropanethiolate, calcium isopropanethiolate, sodium methanethiolate, sodium ethanethiolate, sodium cyclohexanethiolate, potassium methanethiolate, potassium ethanethiolate, ammonium methanethiolate, ammonium ethanethiolate, and combinations of any two or more thereof; and said surfactant is selected from the group consisting of quaternary ammonium salts, alkoxylated compounds, and combinations of any two or more thereof.

13. A process according to claim 1 wherein said aromatic sulfide is 2-chloro-6-nitrophenyl isopropyl sulfide; said halo-substituted aromatic compound is 2,3-dichlorobenzene; said salt of mercaptan is sodium isopropanethiolate; said surfactant is methyltrialkyl($C_8$–$C_{10}$)ammonium chloride which is also known as Adogen® 464; and said aqueous medium is water.

14. A process for producing 2-chloro-6-nitrophenyl isopropyl sulfide comprises contacting, in the presence of methyltrialkyl($C_8$–$C_{10}$)ammonium chloride, 2,3-dichloronitrobenzene with sodium isopropanethiolate in an aqueous medium.

15. A process according to claim 1 wherein each of said hydrocarbyl radials has 1 to about 20 carbon atoms.

16. A process according to claim 1 wherein each of said hydrocarbyl radials has 1 to 15 carbon atoms.

17. A process according to claim 1 wherein W is —$NO_2$.

18. A process according to claim 1 wherein said Ar is a phenylene group.

19. A process according to claim 14 wherein said aqueous medium is water.

20. A process according to claim 1 wherein said process is carried out at 65° to 70° C.

21. A process according to claim 1 wherein R is selected from the group consisting of hydrogen, hydrocarbyl radicals each having 1 to 15 carbon atoms, and combinations of any two or more thereof; X is chlorine; W is —$NO_2$; Ar is a phenyl group; R' is an alkyl radical having 1 to 15 carbon atoms; M is an alkali metal; and said surfactant is a quaternary ammonium salt.

22. A process according to claim 21 wherein said process is carried out at 65° to 70° C.

23. A process for producing 2-chloro-6-nitrophenyl isopropyl sulfide comprising contacting,. in the presence of methyltrialkyl($C_8$–$C_{10}$)ammonium chloride, 2,3-dichloronitrobenzene with sodium isopropanethiolate in an aqueous medium and at 65° to 70° C.

* * * * *